(12) United States Patent
Beliczey et al.

(10) Patent No.: US 6,355,453 B1
(45) Date of Patent: Mar. 12, 2002

(54) METHOD FOR MAKING FLUORINATED SUGARS HAVING A SIDE CHAIN AND USE THEREOF

(75) Inventors: Juliane Beliczey, Bergisch Gladbach; Udo Kragl, Kritzmow; Andreas Liese; Christian Wandrey, both of Jülich; Kurt Hamacher, Aachen; Heinz Hubert Coenen, Grevenbroich; Thomas Tierling, Köln, all of (DE)

(73) Assignee: Forschungszentrum Julich GmbH (DE)

( * ) Notice: Subject to any disclaimer, the term of this patent is extended or adjusted under 35 U.S.C. 154(b) by 0 days.

(21) Appl. No.: 09/483,548

(22) Filed: Jan. 14, 2000

Related U.S. Application Data (63) Continuation-in-part of application No. 09/156,322, filed on Sep. 18, 1998, now abandoned.
(51) Int. Cl.$^7$ .................................................. C12P 19/26
(52) U.S. Cl. ........................... 435/84; 435/105; 435/72; 435/137; 536/18.7; 536/55.3; 536/124
(58) Field of Search ........................... 435/84, 105, 72, 435/137; 536/18.7, 55.3, 124

(56) References Cited

PUBLICATIONS

Gautt et al, Biochemistry 3(12):1952–1960, 1964.*

\* cited by examiner

*Primary Examiner*—Francisco Prats
(74) *Attorney, Agent, or Firm*—Connolly, Bove, Lodge & Hutz LLP

(57) ABSTRACT

Furanosides or pyranosides can be reacted with pyruvate and converted into sialic acids in good yields by an enzymatic synthesis, using a suitable aldolase, where the concentration of aldolase, per 50 mM of pyruvate, is 1 to 2,500 U*/ml. For example, 3-fluoroneuraminic acid and other 3,3-didesoxy-3-fluorononulopyranosonic acid derivatives can be prepared in this manner. The F-atom in the resulting sialic acid (which can be $^{19}F$ or $^{19}F$ and $^{18}F$) provides a label which makes possible studies of mammalian physiology and diagnosis of mammalian diseases.

22 Claims, 4 Drawing Sheets

METHOD FOR MAKING FLUORINATED SUGARS HAVING A SIDE CHAIN AND USE THEREOF

This application is a continuation-in-part of U.S. application Ser. No. 09/156,322, filed Sep. 18, 1998, now abandoned.

FIELD OF THE INVENTION

This invention relates to the enzymatic synthesis of fluorinated sugars (including fluorinated amino or amido sugars) which have a cyclic structure and a side chain and hence have a nucleus of more than 6 carbon atoms. An aspect of this invention relates to the synthesis of fluorinated sialic acids or fluorinated nonulosaminic acids, a family of amino sugars containing at least 8, more typically at least 9, carbon atoms.

Another aspect of this invention relates to the enzymatic rid synthesis of 3-fluoroneuraminic acid (5-acetamido-3,5-didesoxy-3-fluoro-D-glycero-D-galacto-nonulopyranosonic acid) and other 3,5-didesoxy-3-fluorononulopyranosonic acid derivatives and their use.

DESCRIPTION OF THE PRIOR ART

The sialic acids are generally cyclic pentoses (furanoses) or cyclic hexoses (pyranoses) with a side chain (typically three carbon atoms long); accordingly, the sugar nucleus of these compounds has 8 or 9 carbon atoms, and this nucleus can be substituted with an amino group which can be in turn be substituted with acyl groups and the like. The most important embodiments of this class of compounds can be considered to be derivatives of amino sugars such as neuraminic acid, $C_9H_{17}NO_8$. At least five sialic acids occur in nature; they are widely distributed throughout the animal kingdom (including some bacteria as well as more complex organisms such as mammals) and appear to be regular components of glycoproteins and glycolipids (where they typically occupy terminal positions). The most important of the sialic acids is generally considered to be the N-acetyl derivative of neuraminic acid ("Neu5Ac"), i.e. 5-acetamido-3,5-dideoxy-D-glycero-D-galacto-nonulopyranosonic acid.

Preparations of sialic acids having 8- as well as 9-carbon nuclei are described in the scientific literature. For an example of a synthesis involving a furanose such as D-arabinose, see U. Kragl et al, *J. Chem. Soc. Perkin. Trans.* 1:119–124 (1994).

Because Neu5Ac and similar sugars occur so widely in higher animals and are so intimately involved in the physiology of mammals, they can be used as diagnostic and investigative tools, provided that they are suitably labeled with an isotope which can be measured or detected by various imaging techniques, radioactivity measurements, and other non-invasive procedures.

Fluorine is one of the most important labeling elements. The stable isotope, $^{19}F$, provides opportunities for in vivo investigation with $^{19}F$-NMR spectroscopy and has advantages over $^1H$-NMR spectroscopy used in MR-tomography. In the body, fluorine occurs naturally only in teeth and bones. Therefore, it is possible to observe the kinetics of the biodistribution of fluorine-labeled compounds.

Fluorine has several isotopes in addition to $^{19}F$, all of which are unstable, but only one of these has practical significance: the isotope, $^{18}F$, which is radioactive and has the longest half-life of the unstable isotopes (the other unstable isotopes have half-lives lasting less than 3 minutes). The $^{18}F$ isotope has a half-life of 110 minutes and is very useful in biological studies and in medicine, but a half-life of less than 2 hours does impose some limits on its utility. Examples of the uses of $^{18}F$ include non-invasive measurement of pharmacokinetic phenomena and the localization of tumors with $^{18}F$-labeled 2-fluorodesoxyglucose (e.g. by positron emission tomography).

The short half-life of the $^{18}F$ isotope can impose severe requirements upon methods for synthesizing the $^{18}F$-labeled compound. The yield of labeled compound should be high, and, even more important, the synthesis must be very rapid.

In any method in which an F-labeled compound is used, it is generally necessary that its physiological properties (e.g. its properties as a substrate for an enzyme) be similar to the endogenous, non-fluorinated compound it is supposed to mimic. The fluorine atom has the advantage of being fairly small in its covalent radius and hence does not differ too markedly from hydrogen in terms of steric hindrance. A fluorine substituent does differ from other substituents in terms of charge density, due to its high electronegativity and electronic density. But generally speaking, the advantages of fluorine as a labeling substituent far outweigh its disadvantages.

A number of F-labeled derivatives of Neu5Ac are known. For example, the 3-fluorine derivative ("Neu5Ac3F"), which has the systemic name 5-acetamido-3,5-didesoxy-3-fluoro-D-glycero-D-galacto-nonulopyranosonic acid, can be prepared by the aldol condensation of N-acetylmannosamine ("ManNAc") and fluoropyruvate or β-fluoropyruvic acid (F—$CH_2$—CO—COOH, systemic name 1-fluoro-2-oxopropanoic acid). The yield, however, is moderate (1.5%) and the purification is labor intensive. A recent paper discloses an electrophilic selective fluorination which provided yields up to 80% and diastereomer selectivity of 75%. But the need for a faster and more stereospecific synthesis still exists.

The biosynthesis of Neu5Ac is enzyme-catalyzed and would appear to provide a model for a quick synthesis. In the biosynthesis, ManNAc is reacted with the pyruvate (pyruvic acid, $CH_3$—CO—COOH), and the enzyme catalyst is N-acetylneuraminic acid aldolase. N-acetylneuraminic acid aldolase EC 4.1.3.3 can be found in animal tissue and some bacteria. This enzyme has also been produced by biotechnology methods involving common microorganisms such as *E. coli*. The natural sialic acid Neu5Ac has been made successfully by enzymatic synthesis, but the preparation of Neu5Ac derivatives (particularly Neu5Ac3F) is more problematic.

The enzymatic synthesis of Neu5Ac3F has been investigated. For example, the amounts of substrates (the sugar component, ManNAc, and the pyruvate, β-fluoropyruvate) have been varied considerably. The ManNAc would be expected to react with the β-fluoropyruvate ("F-pyr") to form Neu5Ac F-substituted at the 3-position (Neu5Ac3F), but under the conditions chosen in the If literature (50 mM of both substrates, 0.1 U*/ml and N-acetylneuraminic acid aldolase ["Neu5Ac-aldolase"] from *E. coli* in water, buffered at a pH of 7.7, maintained at 37° C. and incubated for 24 hours), no conversion to Neu5Ac3F was observed. (The expression U*, a convenient enzyme activity unit employed in presenting data hereafter, was devised by the enzyme supplier, Toyobo, and is the enzyme activity with respect to the standard reaction of "Pyr" (pyruvate)+ManNAc to obtain Neu5Ac. The expression U [without the asterisk], also used hereafter, is the enzyme activity with respect to the reaction of F-Pyr+ManNAc to Neu5Ac3F.)

Accordingly, further investigation of the enzymatic synthesis of these fluorinated sugars (particularly fluorinated amino sugars such as Neu5Ac3F) is needed.

SUMMARY OF THE INVENTION

It has now been discovered that the manipulation of enzyme synthesis conditions can provide a high-yield and preferably rapid preparation of fluorinated $\geq$8-carbon sugars from the appropriate substrates using an aldolase enzyme. First and foremost, the enzyme concentration must be increased drastically in comparison to the concentration reported in the literature. This drastic increase in enzyme concentration does not create any serious economic drawback. The enzyme obtained through biotechnology methods, e.g. from *E. Coli*, is relatively inexpensive. The enzyme Neu5Ac-aldolase from *C. perfringens* is also commercially available and can be used in this invention with results similar to the enzyme from *E. coli*. Moreover, the enzyme exhibits remarkable stability and can be recovered and reused in subsequent cycles or batches.

To insure that the synthesis will be fast enough to permit the use of $^{18}$F-labeled compounds, the sugar component is preferably present, in molar terms, in a large excess by comparison to the fluorinated component. The fluorinated component concentration should be sufficient also, however, and it is preferred, in the synthesis of $^{18}$F-labeled compounds, to introduce a significant amount of $^{19}$F-containing substrate as a carrier.

For cost-effectiveness, the synthesis is carried out on a scale in which the amounts of substrates are in the tens or hundreds of millimoles. Aldolase enzyme activity peaks within the range of 30–60 mM of F-pyr and generally increases with increasing amounts (e.g. >300, preferably >400 mM) of the sugar. The aldolase enzyme concentration is preferably in excess of 1 U*/ml and can range as high as 2,500 U*/ml. When the amount of F-Pyr is within the desired range (e.g. about 50 mM), the preferred aldolase enzyme concentration is 20 to 500 U*/ml, 100 to 200 U*/ml being especially preferred. Further, the reaction can also depend on temperature and pH. The preferred temperature range from about 1° C. to about 55° C. The preferred pH can range from about 5 to about 10.

BRIEF DESCRIPTION OF THE DRAWING

The principles of this invention are illustrated by the accompanying Drawings, wherein the results of several kinetic studies are shown graphically. The first three kinetic studies were carried out with 24 U*/ml (24 U*/mg enzyme lyophilisate). The enzyme activity was measured as a function of the substrate concentrations and the product concentration.

Thus.

Since Neu5Ac3F can exist in the form of stereoisomers, and the aldolase produces two diastereomers (though not in equal amounts, the relative amounts being dependent upon reaction conditions), an additional study was done to investigate the effect of the reaction conditions on the relative amounts of the two diastereomers.

Thus.

As noted previously, the aldolase enzyme is reasonably stable and can be recovered and reused.

Thus.

DETAILED DESCRIPTION

In the case of the preferred pyranose starting materials, the reaction which is facilitated to a surprising degree by this invention can be represented in general terms as Reaction 1 ("Rx 1"):

where R is OH or a nitrogen-containing group such as amino or amido, and M$^+$ is H$^+$ or a pharmaceutically-acceptable cation.

As indicated above, substrate (I) is a sugar or amino sugar typically having a Haworth-Hirst pyranoside nucleus. However, substrate (I) can also be a furanoside. Substrate (II) is the fluoropyruvate (F-pyr), and product (III) has a fluorine label and a nine-carbon nucleus. The R group can increase the total number of carbons. For example, if R is —NH—CO—CH$_3$, the total number of carbons in the product would be 11.

Although amino sugars are preferred as substrate (I), mannose (a hexose in which R=OH) has been successfully converted with F-pyr in accordance with this invention to obtain ketodesoxy-nonulopyranosonic acid ("F-KDN").

Pyranosides and compounds derived from them such as sialic acids generally have rings with the "chair" configuration of cyclohexane, and like cyclohexane, the rings can have axial and equatorial substituents. In the case in which substrate (I) is ManNAc but substrate (II) is pyruvic acid, the resulting product (Neu5Ac) has no stereoisomerism at the 3-position. But when F-pyr is substrate (II), the two substituents at the 3-position are not the same, and the F-substituent can be oriented either axially or equatorially. This steric effect is illustrated by Reaction 2 ("Rx 2"), in which substrate (I) is ManNAc (shown in the chair configuration) and substrate (II) is F-pyr; "Ac" represents the acetyl group, CH$_3$CO—, hence -NHAc is the acetamido group, —NH—CO—-H$_3$:

known to those skilled in the art, e.g. by elution from an ion exchange medium.

Figure 2:
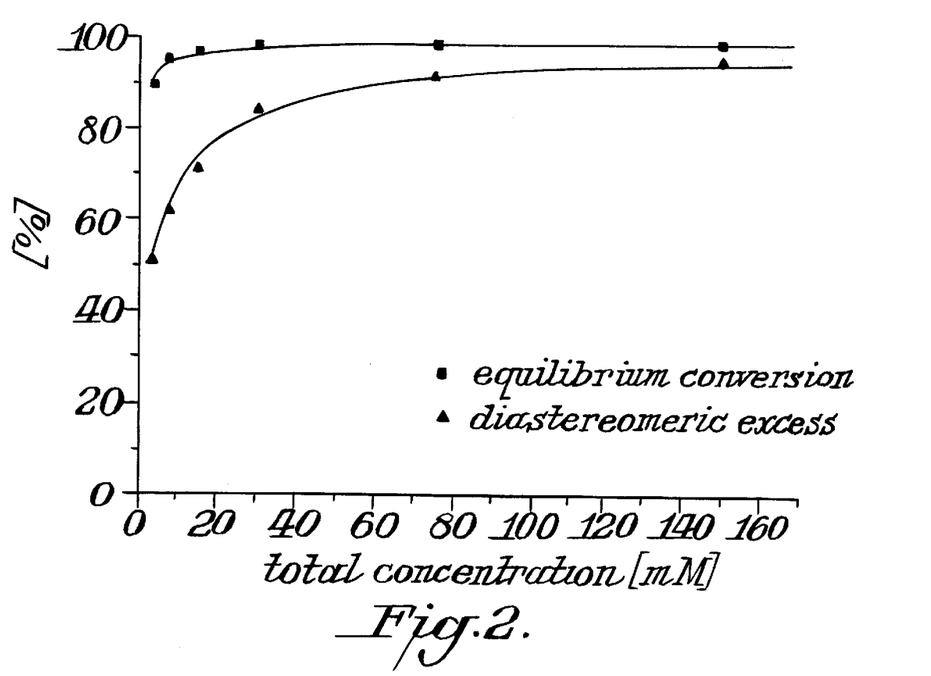
FIG. 2 is a plot of diastereometric excess (excess of the diastereomer favored by the enzyme synthesis) and equilibrium conversion as a function of the total concentration (in mM), i.e. ManNAc+Neu5Ac3F with equal concentrations of substrates (F-pyr=ManNAc); the equilibrium constant $(K_{eq})$=8500±5600 l/mol.

FIG. 2 shows the dependence of the equilibrium position (% of equilibrium conversion) and the diastereomeric excess upon total concentration ([ManNAc]+[Neu5Ac3], with [F-pyr]=[ManNAc]).

Figure 1A:
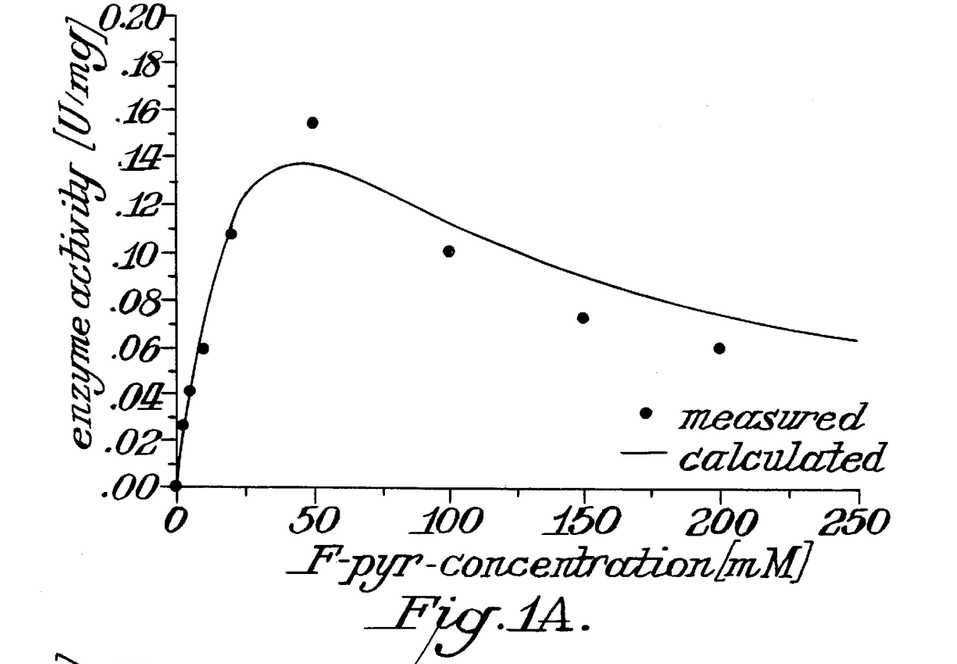
FIG. 1A is a plot of enzyme activity as a function of the fluoropyruvate (F-pyr) concentration (in mM), under the following conditions: 24 U*/ml (1 mg/ml) of the aldolase enzyme; 300 mM of the other substrate, N-acetylmannosamine (ManNAc); a pH of 7.5; and a temperature of 25° C.
Figure 1B:
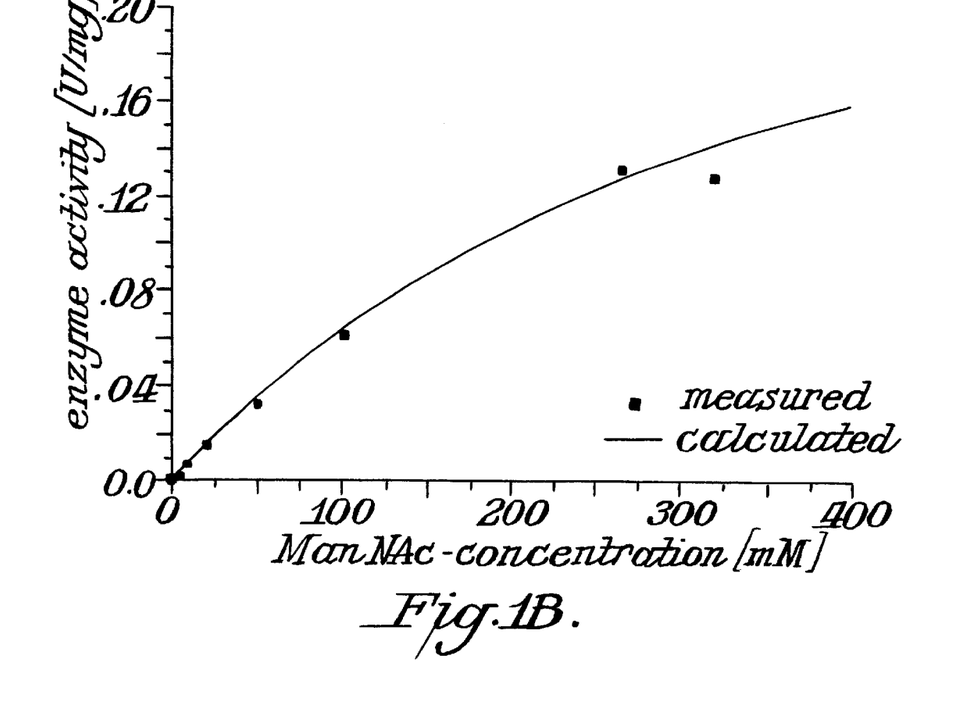
FIG. 1B is a plot of enzyme activity as a function of the ManNAc concentration (in mM); in this case the F-pyr substrate is present at a concentration of 50 mM; the amount of aldolase is 24 U*/ml (1 mg/ml); and the pH and temperature are again 7.5 and 25° C., respectively.
Figure 4:
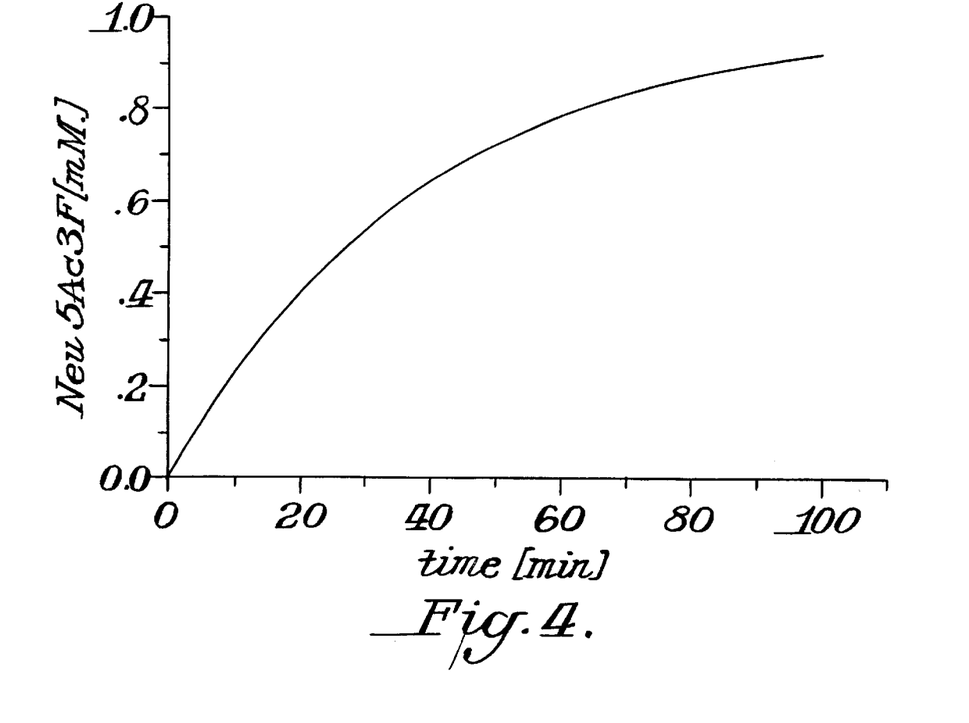
FIG. 4 illustrates a rapid conversion of [$^{18}$F]F-Pyr tracer with [$^{19}$F]F-Pyr and ManNAc to Neu5Ac3F (mM of Neu5Ac3F produced vs. time in minutes), where the ManNAc substrate is in large excess (125 mM) compared to the F-pyr (1 mM [$^{19}$F]F-Pyr with 100–300 $\mu$Ci of [$^{18}$F]F-Pyr). Other conditions: aldolase=125 U/ml (5 mg/ml), pH=7.5, and temperature=25° C. The equilibrium conversion was >99%.
Figure 5:
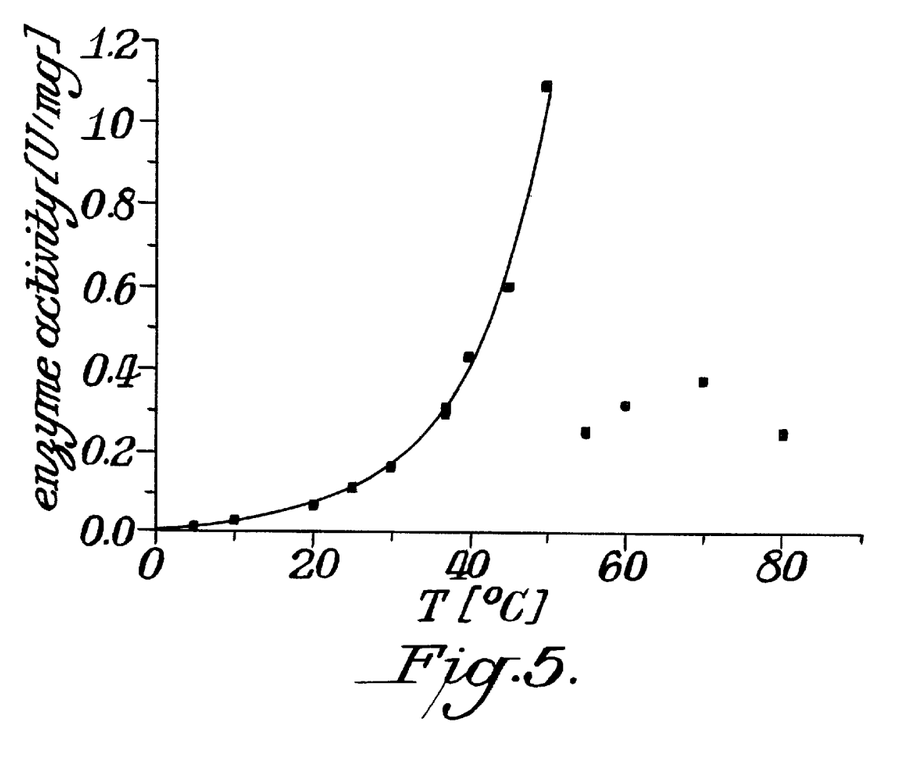
FIG. 5 illustrates enzyme activity as a function of temperature with pH=7.5, [ManNAc]=400 mM, [F-Pyr]=50 mM and Aldolase=1 mg/ml.

As noted previously, equality of concentration of the two substrates is not necessarily ideal, particularly if a rapid synthesis is desired. FIG. 1A illustrates a kinetic study carried out at various F-pyr concentrations with the ManNAc concentration set at 300 mM, and FIG. 1B illustrates the effect of ManNAc concentration when the F-pyr concentration is set at 50 mM. FIGS. 1A and 1B (and cf. FIG. 4) suggest that the concentrations of each substrate are important variables affecting enzyme activity. The kinetic study in FIG. 1A is considered to demonstrate that a concentration of 30–60, preferably 40–50, mM F-Pyr leads to the highest enzyme activity. FIG. 1B is considered to show that the enzyme activity also increases with increasing ManNAc concentration, and a ManNAc concentration greater than 300 mM, preferably >400 mM, is desirable.

Enzyme kinetics is a very useful tool for providing insights into enzyme-catalyzed reaction mechanisms. The (Rx 2)

When Rx 2 is carried out under the conditions employed in this invention, the amount of diastereomer with the fluorine substituent in the axial position ("axial-F diastereomer") far exceeds the diastereomer with the equatorial fluorine substituent ("equatorial-F diastereomer"). The ratio of axial-F:equatorial-F is influenced by the reaction conditions (total concentration, substrate ratio, enzyme concentration). Via $^{19}$F-NMR spectroscopy, it can be shown that the axial-F diastereomer is formed in excess at a total of concentration of >3 mM.

The axial diastereomer, which is the main product and is mixed with a relatively small amount of the byproduct (the equatorial-F diastereomer) can be purified by methods well simplest case, where a free enzyme and a single substrate form an enzyme-substrate complex which reverts back to free enzyme+substrate and/or forms products, can be described in an equation which relates the velocity of the reaction (v) to total enzyme concentration (free enzyme concentration+concentration of complexed enzyme), substrate concentration, rate constants, and the Michaelis constant ($K_m$). This approach has been successfully extended to more complicated enzyme-catalyzed reactions in which more than one substrate is present. Using an equation that describes—in the "standard" ManNAc/Pyr reaction—the dependence of the reaction velocity (and hence the enzyme activity) upon the substrate concentrations $c_{(pyr)}$ and $c_{(ManNAc)}$ and the product concentration $c_{(Neu5Ac)}$, an equation can be modeled for reaction velocity or enzyme activity in the seemingly analogous fluorine-labeling reaction between ManNAc and F-pyr. The resulting model kinetic equation ("Equation 1") is set forth subsequently. Like the equation for the standard, ManNAc/Pyr reaction, the concentration value $c_{(ManNAc)}$ is used, but the concentration values of the other substrate, i.e. $c_{(F-pyr)}$, and the product, $c_{(Neu5Ac3F)}$, are taken from the ManNAc/F-pyr reaction. The kinetic parameters of Equation 1 were determined from data measured under initial reaction conditions by means of non-linear regression. Among the kinetic parameters of the model equation are the $K_m$ values for F-pyr and ManNAc. The $K_m$ value for ManNAc (393 mM) matches well with the value given in the literature for the standard, ManNAc/Pyr reaction (402 mM). The $K_m$ value for F-pyr (41 mM) is about 5 times higher than the one for the standard reaction (8.5 mM) and additionally a substrate surplus inhibition is observed.

Equation 1 is given below:

$$V=(a*b*v_{max})/((a+(a^2/K_{ia})+(K_{ma}*(1+(P/K_{ip}))))*(b+K_{mb}*(1+(P/K_{ip}))))$$

where:

$V_{max} = 0.898 \pm 0.347$ U/mg
$a = c_{(F-Pyr)}$ mM  $K_{ma} = 41 \pm 20$ mM  $K_{ia} = 49 \pm 25$ mM
$b = c_{(ManNAc)}$ mM  $K_{mb} = 393 \pm 168$ mM
$P = C_{(Neu5Ac3F)}$ mM  $K_{ip} = 644 \pm 123$ mM, and where the kinetic parameters referred to above are $V_{max}$ (maximal reaction rate), $K_{ma}$ ($K_m$-value of F-Pyr), $K_{mb}$ ($K_m$-value of ManNAc), $K_{ia}$ (substrate surplus inhibitor constant for F-pyr) and $K_{ip}$ (product inhibitor constant of Neu5Ac3F). In the foregoing equation, an asterisk is used to indicate a product (i.e. x*y means the product of x and y).

The differences between the standard, ManNAc/Pyr reaction and the ManNAc/F-pyr reaction have important consequences. While the maximal activity of the standard reaction reaches 13.8 U/mg (with an enzyme charge of >15 U*/mg), the maximal activity of the reaction with F-pyr is reduced to 0.9 U/mg (with an enzyme charge of >24 U*/mg). This is an explanation for the observation in the literature (Y. Uchita et al., *J. Biochem*. 96: 507–514 [1984]) that no conversion took place. The concentration of 50 mM F-pyr is well chosen in view of the $K_m$-value and the substrate surplus inhibition of F-pyr, but the 50 mM concentration of ManNAc is far below the mi-value of 393 mM. At the 50 mM concentration, only an activity of 0.035 U/mg of enzyme (with 24 U*/mg) is reached, which corresponds to 1/685 part of the applied enzyme activity. With a standard activity of 0.1 U*/ml this would correspond to an activity of $1.46*10^{-4}$ U/ml. With the definition for one unit, 1 U=1 $\mu$mol/min; this results in a product formation of $1.46*10^{-4}$ $\mu$mol*(min*ml)$^{-1}$ or 0.21 $\mu$mol*(d*ml)$^{-1}$ (see the foregoing 5 description of the use of the asterisk to indicate products).

FIG. 1B confirms that enzyme activity increases with increasing (ManNAc):(F-pyr) and that the ManNAc concentration should be well in excess of 50 mM. FIG. 1A confirms that 50 mM is a good choice for the concentration of the F-pyr substrate.

Figure 1C:
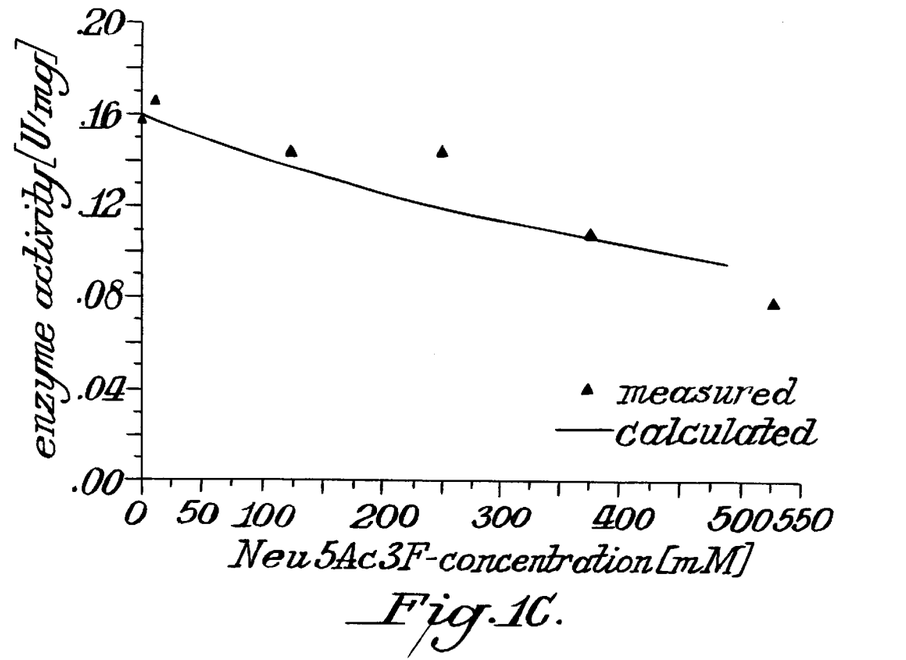
FIG. 1C is a plot of enzyme activity as a function of Neu5Ac3F concentration in mM; the aldolase was again 24 U*/ml (1 mg/ml); the ManNAc substrate concentration was 300 mM; the F-pyr substrate concentration was 50 mM; the pH was 7.5; and the temperature was 25° C.

Some loss of enzyme activity occurs as the product concentration increases (see FIG. 1C), but enzyme activity losses can be compensated for.

Although F-pyr is typically F—CH$_2$—CO—COOH, the synthesis of this invention can take place under mildly basic conditions, under which F-pyr can be F—CH$_2$—COO$^{-}$ $M^{+}$, where $M^+$ is H$^+$and/or a pharmaceutically acceptable cation such as an alkali metal cation.

The invention is further illustrated by the following non-limiting Examples.

EXAMPLE 1

Recovery and Reuse of Enzyme in Repeated Cycles

The substrates ManNAc and F-pyr were incubated at a concentration of 200 mM and an enzyme concentration of 8 mg/ml (192 U*/ml) at 25° C. and pH 7.5. After the reaction was completed, the solution was centrifuged in an Amicon Centriprep under retention of the enzyme by an ultrafiltration membrane. Thereafter, a new substrate solution was added to the enzyme. Due to the loss of activity by the filtration step, 4 mg/ml enzyme were added every 3 cycles.

Figure 3:
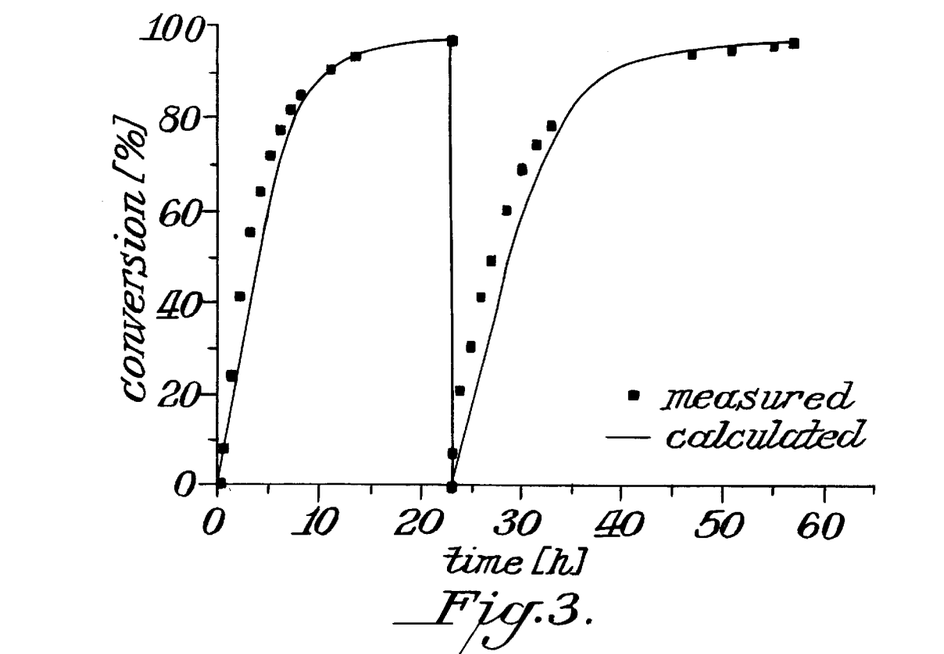
FIG. 3 illustrates the performance (% conversion vs. time in hours) of repetitive batches where the substrate concentrations were equal (ManNAc=F-pyr=200 mM), but the aldolase was much higher (192 U*/ml (8 mg/ml); pH=7.5; temperature=25° C. Enzyme had to be added to compensate for deactivation (33%), and the diastereometric excess was 91%.

From 6 cycles, 2 g product were isolated with a diastereomeric excess of 91%. The course of the two first cycles is shown in FIG. 3. The purification of the main-product (F-axial) was achieved with an anion exchanger (Dowex 1X2 formate form, elution with formic acid gradient 0→1 molar).

EXAMPLE 2

Labeling With $^{18}$F (Rapid Synthesis)

Neu5Ac3[$^{18}$F]F was produced by an enzyme synthesis using the substrates [$^{18}$F]F-pyr and ManNAc in the presence of [$^{19}$F]F-pyr as a carrier. Because of the need of a fast conversion in the enzyme reaction due to the short half-life of the $^{18}$F, a sufficient substrate concentration is necessary. Therefore 1 MM a [$^{19}$F]F-pyr was added to the [$^{18}$F]F-pyr as carrier. For the same reason, ManNAc was applied in a high excess of 125 mM. The assigned radioactivity was 100–300 $\mu$Ci which corresponds to a radioactivity concentration of nano- to picomolar. The enzyme concentration was 5 mg/ml. By using the kinetic model (Equation 1) the conversion time course shown in FIG. 4 could be simulated. A quantitative measurement was not possible with the available analytic technique, because of an inadequate baseline.

EXAMPLE 3

Mannose And F-pyr As Substrates

Mannose was also successfully converted with F-pyr to F-KDN (ketodesoxynonulo-pyranosonic acid). Again both epimers are formed in different amounts (axial epimer >95%). The reaction is slower than the ManNAc/F-pyr reaction and the conversion attained is smaller. The quantification was difficult, however, due to the poor UV activity of both substrates and the product. Under the same conditions as in Example 1, in two repetitive reaction cycles, 500 mg product were synthesized.

COMPARATIVE EXAMPLES

A. (ManNAc)=(F-pyr)=50 mM, And Low Enzyme Activity

The work of Y. Uchita et al. was repeated under the conditions reported in that paper, and the same results were observed. Measurable conversion to Neu5Ac3F was not observed.

B. ManNAc+β-Hyroxypyruvate

An attempt was made to substitute β-hydroxypyruvate for F-pyr. The experiment showed that a conversion of β-hydroxypyruvate (unlike F-pyr) takes place only to a very small extent. When interacting with Neu5Ac, the hydroxy radical differs significantly from hydrogen not only in electron density but in size as well. Apparently the steric factor plays a much larger role in this reaction than in the ManNAc/F-pyr reaction.

C. ManNAc+β-Bromopyruvate

The attempt to substitute bromopyruvate for fluoropyruvate was not successful. Conversion of bromopyruvate was not observed.

We claim:

1. An enzymatic synthesis of a fluorinated sugar having at least 8 carbon atoms, said synthesis comprising reacting a F—CH$_2$—CO—COO$^-$M$^+$ with a furanoside or pyranoside sugar substrate in the presence of an aldolase enzyme, wherein M$^+$ is H$^+$ or a pharmaceutically acceptable cation, and wherein the concentration of aldolase enzyme, per 50 mM of F—CH$_2$—CO—COO$^-$M$^+$, is 1 to 2,500 U*/ml, where U* represents an enzyme activity unit and is the enzyme activity with respect to the standard reaction of pyruvate and N-acetylmannosamine to obtain the N-acetyl derivative of neuraminic acid, further comprising the step of recovering the fluorinated sugar.

2. The synthesis according to claim 1, wherein the amount of the fluorinated sugar produced is sufficient to study mammalian physiology or diagnose mammalian diseases.

3. An enzymatic synthesis according to claim 1 wherein said reaction is represented by the following equation:

wherein R is OH or a nitrogen-containing group, and M$^+$ is a pharmaceutically-acceptable cation.

4. An enzymatic synthesis according to claim 1, wherein the sugar substrate is an amino or amido sugar, and the resulting product is a fluorinated sialic acid.

5. An enzymatic synthesis according to claim 4, wherein said enzyme concentration is about 20 to about 500 U*/ml.

6. An enzymatic synthesis according to claim 1, wherein the sugar substrate is N-acetylmannosamine.

7. An enzymatic synthesis according to claim 1, wherein the sugar substrate is mannose.

8. An enzymatic synthesis according to claim 5, wherein the sugar substrate is N-acetylmannosamine.

9. An enzymatic synthesis according to claim 1, wherein the aldolase enzyme is N-acetylneuraminic acid aldolase E.C. 4.1.3.3.

10. An enzymatic synthesis according to claim 1, wherein the synthesis is a batch process wherein active aldolase enzyme is recovered and reused in subsequent batches.

11. An enzymatic synthesis according to claim 1, wherein the concentration of aldolase enzyme is 100 to 200 U*/ml.

12. An enzymatic synthesis according to claim 1, wherein the reaction medium provides an enzyme activity of at least about 0.02 U/ml, where U represents the enzyme activity with respect to the reaction of said substrates F—CH$_2$—CO—COO$^-$M$^+$ and N-acetylmannosamine to obtain 3-fluoroneuraminic acid.

13. An enzymatic synthesis according to claim 12, wherein said enzyme activity ranges from 0.02 to 1.0 U/ml.

14. An enzymatic synthesis according to claim 8, wherein the product has two diastereomers, an F-axial diastereomer and an F-equatorial diastereomer, and, at the conclusion of the synthesis and without purification, the percentage of the product which is said F-axial diastereomer is about 75 to about 100%.

15. An enzymatic synthesis according to claim 14, wherein said percentage ranges from about 91 to about 98%.

16. An enzyme synthesis according to claim 1, wherein said amount of said fluorinated sugar, which comprises axial-F and equatorial-F diastereomers, is taken up in an ion exchange medium and purified or separated into separate yields of axial-F and equatorial-F diastereomers.

17. A method for studying physiology or diagnosing disease states in mammals, comprising:
(a) synthesizing a fluorinated sugar having at least 8 carbon atoms by reacting, in a reaction medium, a F—CH$_2$—CO—COO$^-$M$^+$ with a furanoside or pyranoside sugar substrate in the presence of an aldolase enzyme, wherein M$^+$ is H$^+$ or a pharmaceutically acceptable cation, and wherein the concentration of aldolase enzyme, per 50 mM of F—CH$_2$—CO—COO$^-$M$^+$, is 1 to 2,500 U*/ml, where U* represents an enzyme activity unit and is the enzyme activity with respect to the standard reaction of pyruvate and N-acetylmannosamine to obtain the N-acetyl derivative of neuraminic acid;
(b) administering the fluorinated sugar to a mammal; and
(c) monitoring the biodistribution or the pharmacokinetics of said fluorinated sugar in said mammal.

18. A method according to claim 17, wherein the fluorinated sugar of said step (a) is administered to the mammal without separating the fluorinated sugar from the reaction medium.

19. A method according to claim 17, wherein the fluorinated sugar of said step (a) is isolated from the reaction medium before it is administered to the mammal.

20. An enzymatic synthesis of a fluorinated sugar having at least 8 carbon atoms, said synthesis comprising reacting a F—CH$_2$—CO—COO$^-$M$^+$ with a mannose substrate in the presence of an aldolase enzyme, wherein M$^+$ is H$^+$ or a pharmaceutically acceptable cation, and wherein the concentration of aldolase enzyme, per 50 mM of F—CH$_2$—CO—COO$^-$M$^+$, is 1 to 2,500 U*/ml, where U* represents an enzyme activity unit and is the enzyme activity with respect to the standard reaction of pyruvate and N-acetylmannosamine to obtain the N-acetyl derivative of neuraminic acid.

21. An enzymatic synthesis of a fluorinated sugar having at least 8 carbon atoms, said synthesis comprising reacting a F—CH$_2$—CO—COO$^-$M$^+$ with a furanoside or pyranoside sugar substrate in the presence of an aldolase enzyme, wherein M$^+$ is H$^+$ or a pharmaceutically acceptable cation, wherein the synthesis is a batch process wherein active aldolase enzyme is recovered and reused in subsequent batches, and wherein the concentration of aldolase enzyme, per 50 mM of F—CH$_2$—CO—COO$^-$M$^+$, is 1 to 2,500 U*/ml, where U* represents an enzyme activity unit and is the enzyme activity with respect to the standard reaction of pyruvate and N-acetylmannosamine to obtain the N-acetyl derivative of neuraminic acid.

22. An enzymatic synthesis of a fluorinated sugar having at least 8 carbon atoms, said synthesis comprising reacting a F—$CH_2$—CO—$COO^-M^+$ with a furanoside or pyranoside sugar substrate in the presence of an aldolase enzyme, wherein $M^+$ is $H^+$ or a pharmaceutically acceptable cation, wherein said amount of said fluorinated sugar, which comprises axial-F and equatorial-F diastereomers, is taken up in an ion exchange medium and purified or separated into separate yields of axial-F and equatorial-F diastereomers, and wherein the concentration of aldolase enzyme, per 50 mM of F—$CH_2$—CO—$COO^-M^+$, is 1 to 2,500 U*/ml, where U* represents an enzyme activity unit and is the enzyme activity with respect to the standard reaction of pyruvate and N-acetylmannosamine to obtain the N-acetyl derivative of neuraminic acid.

* * * * *